United States Patent [19]

DeAntonio et al.

[11] Patent Number: 4,994,025
[45] Date of Patent: Feb. 19, 1991

[54] METHOD OF DISSOLVING CHOLESTEROL-RICH CALCULI WITH SHORT CHAIN HALOGENATED ORGANIC SOLVENTS AND COSOLVENTS

[75] Inventors: Paul DeAntonio, Westminster; Kenneth G. Mayhan, Irvine; John T. Sorensen, Costa Mesa, all of Calif.

[73] Assignee: Baxter International Inc., Deerfield, Ill.

[21] Appl. No.: 400,212

[22] Filed: Aug. 29, 1989

[51] Int. Cl.$^5$ ............................................... A61M 1/00
[52] U.S. Cl. ...................................... 604/28; 604/49; 604/27
[58] Field of Search ................ 128/24 EL; 604/28, 48, 604/51, 27, 49

[56] References Cited

U.S. PATENT DOCUMENTS

| | | | |
|---|---|---|---|
| 4,517,309 | 5/1985 | Noda | 514/376 |
| 4,655,744 | 4/1987 | Thistle et al. | 604/152 |
| 4,696,668 | 9/1987 | Wilcox | 604/28 |
| 4,755,167 | 7/1988 | Thistle et al. | 604/22 |
| 4,845,125 | 7/1989 | Geier | 128/24 EL |
| 4,902,276 | 2/1990 | Zakko | 604/28 |

Primary Examiner—Stephen C. Pellegrino
Assistant Examiner—Michael Rafa
Attorney, Agent, or Firm—Sandra S. Schultz; Michael C. Schiffer

[57] ABSTRACT

Disclosed is a method for dissolving cholesterol-rich calculi, most preferably gallstones in vivo, comprising contacting the calculus with a fluid compound of the formula R-X, R having 2 to 4 carbon atoms with substituents consisting of hydrogen of halogen, X being halogen, and wherein if X is fluorine, at least one substituent is selected from the group consisting of hydrogen, chlorine, bromine, or iodine. Usually R-X is 2-bromo-2-chloro-1,1,1-trifluoroethane (also referred to as Halothane.) Other compounds of particular interest are 2-chloro-1,2,-dibromo-1,1,2-trifluoroethane, 1-bromo-2-chloro-1,1,2-trifluoroethane, 2,3-dibromo-1,1,1-trifluoropropane, 2-iodo-1,1,1-trifluoroethane, 1,2-dichloro-1,1-difluoroethane, 1,1,2-trichloro-2,3,3-trifluorocyclobutane, hexafluoro-1,1,3,4,-tetrachlorobutane, 1,1,1-trichlorotrifluoroethane, and 1,2-dibromotetrafluoroethane. Furthermore, Halothane and MtBE in combination effectively dissolve cholesterol-rich calculi.

Finally, dissolution can be enhanced by adding to the dissolution solvent up to about 50 percent by volume of a lower alcohol. Usually the lower alcohol is ethanol in the amount of about 5 to 40, usually 10 to 30 and preferably about 10 percent by volume. Most preferably in this case, R-X is Halothane or 1,1,1-trichlorotrifluoroethane. Dissolution using previously known solvents such as MtBE is also enhanced by such addition of lower alcohols. In addition, the practical use of MtBE for dissolution can be improved by the addition of the compounds described above as R-X, particularly Halothane, and usually at levels of about 5 to 50 volume percent Halothane.

17 Claims, No Drawings

4,994,025

METHOD OF DISSOLVING CHOLESTEROL-RICH CALCULI WITH SHORT CHAIN HALOGENATED ORGANIC SOLVENTS AND COSOLVENTS

FIELD OF THE INVENTION

This invention relates to dissolution of cholesterol, in particular cholesterol-rich calculi in vivo.

BACKGROUND OF THE INVENTION

Solidified deposits may develop in hollow organs or ducts within humans and animals and cause numerous health problems, as is known to those skilled in the art. Such deposits include cholesterol-rich gallstones. biliary duct stones in the biliary tract, and cholesterol plaque in the vascular system, for example. These deposits may be removed from the body in various ways, the most common being surgery, particularly in the case of gallstones.

Gallstones are solidified deposits or calculi composed of cholesterol, bilirubin, bilirubin complexes and other components derived from bile. A majority of gallstones have a high cholesterol content distributed through their mass and therefore lend themselves to in vivo dissolution by introduction of a cholesterol dissolving solvent or cosolvent mixture into the area of the body where the calculi are located. In vivo dissolution avoids many of the hazards and complications of surgery, and so is desireable when it can be performed. It has been found to be advantageous, furthermore, to perform the dissolution by repeatedly oscillating or agitating the solvent around the calculi to enhance the dissolution rate. In addition, in the case of gallstones in the gallbladder, it is helpful to withdraw the immiscible bile-solvent mixture periodically in order to renew the cholesterol-bearing solvent and improve stone contact, thus enhancing the dissolution process. This dissolution process is described in U.S. Pat. No. 4,655,744, and apparatus for accomplishing it is described in U.S. Pat. No. 4,723,941, both of which are incorporated by reference fully herein.

However, in order for in vivo dissolution of cholesterol-rich calculi to be functional, effective solvents must be located and used. This is a difficult matter, and numerous researchers have evaluated solvents, largely unsuccessfully, for such purposes over the past few years. Large numbers of solvents have been tried, and only three are commonly recognized as particularly effective: diethyl ether, monooctanoin, and methyl tertiary-butyl ether ("MtBE"). Monooctanoin, according to the literature, dissolves between about 12 to 23 grams of cholesterol per deciliter of solvent at 37° C.; our measurements (some are set forth later) indicate that MtBE dissolves about 24 grams of cholesterol per deciliter of solvent at 30° C., and that diethyl ether dissolves about 27 grams of cholesterol per deciliter solvent at 30° C.

Each, however, does present certain problems associated with its use. For example, diethyl ether's normal boiling point, 34.6° C., is so low that it converts into a gas when introduced into the body for dissolution, and it is very flammable. Monooctanoin, on the other hand, has such a high viscosity that dissolution occurs very slowly, taking days or weeks to accomplish in vivo. MtBE, on the other hand, is fairly effective, dissolution sometimes being accomplishable in a day, but it is highly flammable so that a great deal of care must be exercised when purifying and using it. Further, because MtBE is immiscible with bile and has a lower density than bile, and because gallstones have a higher density than bile, MtBE floats on bile-encompassed gallstones, thus making solvent-gallstone contact difficult, particularly without agitation or mixing.

It would be desireable to develop a broader group of solvents usable for such dissolution processes which avoid at least some of the difficulties associated with the solvents now known to be effective.

SUMMARY OF THE INVENTION

The present invention solves many of the problems asssociated with prior solvents for dissolution of cholesterol-rich calculi. In one aspect, the invention is a method for dissolving cholesterol-rich calculi comprising contacting the calculus with a fluid compound of the formula R-X, R having 2 to 4 carbon atoms with substituents consisting of hydrogen or a halogen, X being halogen, and wherein if X is fluorine, at least one substituent is selected from the group consisting of hydrogen, chlorine, bromine, or iodine. Usually R is alkyl or cycloalkyl, and R-X is most preferably 2-bromo-2-chloro-1,1,1-trifluoroethane (hereafter sometimes referred to as Halothane). Other preferred compounds are 2-chloro-1,2,-dibromo-1,1,2-trifluoroethane, 1-bromo-2-chloro-1,1,2-trifluoroethane, 2,3-dibromo-1,1,1-trifluoropropane, 2-iodo-1,1,1-trifluoroethane, 1,2-dichloro-1,1-difluoroethane, 1,1,2-trichloro-2,3,3-trifluorocyclobutane, hexafluoro-1,1,3,4,-tetrachlorobutane, 1,1,1-trichlorotrifluoroethane, and 1,2-dibromotetrafluoroethane.

Generally the cholesterol-rich calculi are selected from the group consisting of gallstones in the gallbladder, gallstones and biliary duct stones in the biliary tract, and plaque in the vascular system. Agitation of the solvents and aspiration of bile plus solvent(s) in the gallbladder may be used to enhance in vivo dissolution of gallstones.

In another aspect, the invention is a method for dissolving cholesterol-rich calculi comprising contacting the calculi with a fluid composition comprised of the following: (a) a fluid compound of the formula R-X. R having 2 to 4 carbon atoms with substituents consisting of hydrogen or halogen, X being halogen, and wherein if X is fluorine, at least one substituent is selected from the group consisting of hydrogen, chlorine, bromine, or iodine, and (b) up to about 40 percent by volume of a "lower alcohol" (i.e. an alcohol having 1 to 4 carbons). Usually R is alkyl or cycloalkyl and the lower alcohol is ethanol in the amount of about 5 to about 30 percent by volume. Most preferably, R-X is Halothane or 1,1,1-trichlorotrifluoroethane (when appropriate sometimes hereafter referred to as Freon TF, which is a DuPont trademark for the compound), but it is usually any of the compounds mentioned above. Usually the cholesterol calculi are gallstones, biliary duct stones, or plaque, most preferably gallstones.

In another aspect, the invention is a method for dissolving cholesterol calculi, most preferably gallstones, with a composition comprising a mixture of MtBE and R-X as defined above, usually MtBE and Halothane, preferably about 50 to 95 percent by volume MtBE and about 5 to 50 percent by volume Halothane, most preferably about 65-75 volume percent MtBE and about 25-35 volume percent Halothane.

In yet another aspect, the invention is a method for dissolving cholesterol-rich calculi, preferably gallstones, by contacting them with a mixture of MtBE and a lower alcohol as defined above, usually ethanol, and preferably about 80 to 90 percent by volume MtBE and about 10 to 20 percent by volume ethanol.

In a final aspect, the invention is a method of enhancing the dissolution of cholesterol-rich calculi, preferably gallstones in the gallbladder, by contacting them with a lower alcohol cosolvent miscible and mixed with the principal solvent in amounts of about 5 to 40 percent by volume. Preferably the alcohol is ethanol at 10 to 30, most preferably 10 percent by volume.

DESCRIPTION OF THE SPECIFIC EMBODIMENTS

Methods of dissolving cholesterol are detailed in the examples below, as are methods of dissolving cholesterol-rich calculi. Methods of dissolving cholesterol-rich calculi, in particular gallstones in vivo, are also well described in the art cited to the Examiner. In particular, the above-mentioned U.S. patents detail in vivo methods of dissolving gallstones and a particular method is detailed in U.S. patent application Ser. No. 240,992, entitled Multimodal Displacement Pump and Dissolution System for Same, owned by the assignee of the present application. Application Ser. No. 240,992 is incorporated by reference as though fully set forth, and reference is made in particular to pages 23 to 25 thereof. Further detailed discussion of the particular methods of dissolution will therefore be avoided.

The following examples describe in detail the use of compounds and compositions of the present invention found to be effective for the dissolution of cholesterol-rich gallstones. Specifically, compounds and compositions of the formula R-X where X is halogen can be used to dissolve cholesterol and cholesterol-rich calculi. R has 2 to 4 carbons with substituents which are halogen or hydrogen and if X is fluorine, at least one substituent is hydrogen, chlorine, bromine, or iodine. Perfluorinated compounds, as can be seen from the examples, have not to date been found to be successful in such methods.

The compounds discovered above should all effectively dissolve cholesterol or cholesterol-rich calculi although at different rates and amounts. However, solvents usable commercially for in vivo gallstone dissolution at reasonable speeds may require that the equilibrium cholesterol solubility be at least about 4 grams per deciliter of solvent. Furthermore, highly viscous solvents are not kinetically favorable for in vivo dissolution.

Most gallstones have densities less than those of the above-mentioned halocarbon solvents, but greater than that of bile, which is immiscible with and less dense than the above halocarbon solvents. As a result, the cholesterol-rich gallstones tend to float on these halocarbon solvents at the bile-solvent interface. This maintains stone-solvent contact even in the presence of bile, and has been found to enhance in vivo dissolution. Even though the equilibrium solubility of cholesterol in some of the halocarbon solvents may be less than in lower density solvents such as certain ethers, for example MtBE, the rate of dissolution of the cholesterol calculi may be superior in the halocarbon solvents due to such enhanced stone-solvent contact in the presence of bile.

Fluid compounds of particular interest for dissolution are Halothane (frequently commercially availably as a preparation of 2-bromo-2-chloro-1,1,1-trifluoroethane containing 0.01% Thymol as a stabilizer), 2-chloro-1,2,-dibromo-1,1,2-trifluoroethane, 1-bromo-2-chloro-1,1,2-trifluoroethane, 2,3-dibromo-1,1,1-trifluoropropane, 2-iodo-1,1,1-trifluoroethane, 1,2-dichloro-1,1-difluoroethane, 1,1,2-trichloro-2,3,3-trifluorocyclobutane, hexafluoro-1,1,3,4,-tetrachlorobutane, 1,1,1-trichlorotrifluoroethane, and 1,2-dibromo-tetrafluoroethane.

It has also been determined that the addition of a lower alcohol to the above compounds in the amount of about 5 to 40 percent by volume enhances cholesterol and cholesterol-rich calculi dissolution significantly. The preferred alcohol is ethanol and it is preferably added in amounts of about 10 to 30 percent by volume. Those solvents described above as R-X which are lower in cholesterol dissolution level are enhanced to a much greater degree by the addition of a lower alcohol, than are solvents such as Halothane which show high dissolution capacity on their own. Those solvents with lower capacities for cholesterol dissolution are enhanced more with greater amounts of alcohol (such as 10,20, 30, or even 40% by volume), but even Halothane, and MtBE which is already known to be a very effective in vivo gallstone dissolution solvent, are enhanced by the addition of alcohol, although lesser amounts are required. The preferred amount of alcohol, preferably ethanol, to be added to Halothane is about 10% by volume, and the preferred amount to be added to MtBE is about 10 to 20 percent by volume. In fact, ideal compositions for in vivo dissolution seem to have solution capacities for cholesterol of about 10 or more grams per deciliter, which appears to be easily achievable with the addition of the lower alcohols to the above solvent systems. Finally, it has been determined that the addition of MtBE to Halothane enhances Halothane's ability to dissolve cholesterol-rich calculi, and the addition of Halothane to MtBE provides an advantageous solvent by reducing flammability. In fact, the addition of as little as 5 volume percent Halothane to MtBE quenches closed cup combustion and addition of more Halothane improves combustion limits sufficiently to render MtBE a much safer solvent to use.

The following examples illustrate the present invention.

EXAMPLE 1

The following protocol was used to determine the equilibrium cholesterol solubility characteristics of numerous solvents.

Materials: powdered cholesterol constant temperature shaker bath suitable clear glass containers with solvent impermeable lids mortar and pestle Procedure: Powdered cholesterol was melted at 155° C., allowed to cool into a solid and then broken into small pieces using a mortar and pestle. This allows for ease of handling and efficient separation of solvent/cholesterol at equilibrium. 10.00 grams of the cholesterol were then weighed and transferred into clear glass containers with solvent impermeable lids. 10.00 grams of the chosen solvent was weighed and transferred to the bottles containing the cholesterol. Additional amounts of solvents with very high densities were sometimes added to allow a sufficient volume for testing. At these levels, though, the volume of solvent was never capable of completely dissolving the cholesterol present, ensuring a cholesterol-saturated solution.

The containers were then tightly capped and agitated in a constant temperature bath equilibrated to 30° C. for a minimum period of 48 hours with continuous agitation. (Preliminary testing showed that complete cholesterol saturation would be obtained at 24 hours or less). After 48 hours, agitation was halted and the solvent and cholesterol allowed to separate. A known weight of cholesterol-containing solvent was then transferred to a preweighed container and allowed to evaporate in a fume hood. The residual cholesterol was then dried to a constant weight in a vacuum oven at an appropriate temperature and the amount of cholesterol soluble in the solvent calculated and reported in percentage by weight and grams per deciliter. The results were as follows.

| SOLVENT | Cholesterol Solubility | |
|---|---|---|
| | % by Weight | Grams/dl solvent |
| MtBE (for reference) | 24.7 | 24.4 |
| 2-Chloro-1,2-dibromo-1,1,2-trifluoroethane | 8.1 | 19.9 |
| Halothane (2-bromo-2-chloro-1,1,1-trifluoroethane) | 8.1 | 16.5 |
| 1-bromo-2-chloro-1,1,2-trifluoroethane | 6.7 | 13.5 |
| 2,3-dibromo-1,1,1-trifluoropropane | 5.5 | 12.4 |
| 2-iodo-1,1,1-trifluoroethane | 4.5 | 10.0 |
| 1,2-dichloro-1,1-difluoroethane | 5.7 | 8.5 |
| 1,1,2-trichloro-2,3,3-trifluorocyclobutane | 3.9 | 6.5 |
| hexafluoro-1,1,3,4,-tetrachlorobutane | 2.8 | 4.7 |
| Freon TF (1,1,1-trichlorotrifluorothane) | 2.8 | 4.6 |
| 1,2-dibromotetrafluoroethane | 2.0 | 4.4 |
| 1-chloro-1,2,2-trifluorocyclobutane | 2.3 | 3.0 |
| 2,3-dichlorohexafluoro-2-butene | 0.4 | 0.6 |
| 1,2-dichlorohexafluorocyclobutane | 0.3 | 0.5 |
| perfluoroheptane | <0.2 | — |
| perfluorooctane | <0.2 | — |

Conclusion: Halothane and other halogenated compounds having 2 to 4 carbons, with the apparent exception of those completely substituted with fluorine, are generally effective cholesterol dissolution solvents.

EXAMPLE 2

The protocol of Example 2 was used with the following solvent mixtures. The amount of alcohol in the solvent mixture is measured on a volumetric basis.

| Solvent Mixture | Cholesterol Solubility | |
|---|---|---|
| | % by weight | grams/dl solvent |
| 5% methanol in Halothane | 11.6 | 23.9 |
| 5% isopropanol in Halothane | 8.8 | 17.5 |
| 5% t-butanol in Halothane | 9.8 | 19.6 |
| 5% methanol in Freon TF | 5.0 | 8.0 |
| 5% isopropanol in Freon TF | 5.5 | 8.9 |
| 5% t-butanol in Freon TF | 5.8 | 9.5 |
| 10% ethanol in 2-chloro-1,2-dibromo-1,1,2-trifluoroethane | 9.8 | 22.8 |
| 10% ethanol in 1,2-dibromotetrafluoroethane | 6.0 | 12.1 |
| 10% ethanol in hexafluoro-1,1,3,4-tetrachlorobutane | 5.7 | 9.0 |
| 10% ethanol in 1-chloro-2-iodo-1,1,2-trifluoroethane | 8.8 | 18.5 |

Conclusion: The addition of alcohols, particularly 10 to 30, usually 10, percent by volume of lower alcohols such as ethanol, improves the cholesterol solubility characteristics of C2 to C4 halogenated solvents, and significantly improves, possibly optimizes the cholesterol solubility of those solvents with cholesterol solubility characteristics otherwise less than optimum.

EXAMPLE 3

The protocol of Example 1 was used with the following solvent mixtures. The amount of alcohol in the solvent mixture is measured on a volumetric basis.

| Solvent Mixture | Cholesterol Solubility | |
|---|---|---|
| | % by weight | grams/dl solvent |
| 95% ethanol (in H$_2$O) (for reference) | 3.4 | 2.7 |
| 5% ethanol in Halothane | 11.9 | 24.6 |
| 10% ethanol in Halothane | 13.4 | 27.3 |
| 20% ethanol in Halothane | 14.1 | 27.0 |
| 40% ethanol in Halothane | 14.0 | 23.3 |
| 60% ethanol in Halothane | 6.8 | 7.5 |
| 5% ethanol in Freon TF | 3.7 | 7.0 |
| 10% ethanol in Freon TF | 6.4 | 12.0 |
| 20% ethanol in Freon TF | 9.4 | 17.0 |
| 40% ethanol in Freon TF | 11.8 | 19.2 |
| 60% ethanol in Freon TF | 10.5 | 12.2 |
| 0% ethanol in MtBE (for reference) | 24.7 | 24.4 |
| 2% ethanol in MtBE | 28.8 | 30.0 |
| 10% ethanol in MtBE | 34.3 | 38.8 |
| 20% ethanol in MtBE | 31.9 | 35.1 |
| 30% ethanol in MtBE | 29.8 | 32.0 |
| 40% ethanol in MtBE | 23.0 | 24.5 |

Conclusion: Amounts of alcohol to be added to the base solvent for optimum performance varies; better solvents originally are optimized with less alcohol than less optimum solvents. Solubility of cholesterol in Halothane, for example, which is one of the optimum cholesterol solvents, is optimized at about 10 to 30 volume percent ethanol.

EXAMPLE 4

An experiment was conducted in order to verify the solubility of human gallstones, rich in cholesterol, in solvents chosen due to their success in dissolving stones of melted and solidified cholesterol, as described above.

Procedure: Explanted human gallstones from the same gallbladder, selected due to their richness in cholesterol, were placed individually into 10.00 grams of the solvents listed below. Each stone weighed between 0.20 and 0.30 grams and was about the size of a pea. All of the stones contained dark areas assumed to be something other than cholesterol. The stones and solvents were sealed in clear glass sample jars and were gently agitated in a 30° C. constant temperature bath for a total of approximately 40 hours. At the end of the 40 hour period, the sample jars were removed from the bath and visual observations made as to the degree of dissolution. It is our experience that with cholesterol-rich gallstones, when sufficient cholesterol has dissolved, the remaining structure fragments and ultimately collapses. The dissolution process of human gallstones is easily observed with in vitro experiments. The number and types of fragments recovered after in vivo dissolution experiments are observed to be generally the same as those from in vitro experiments.

Halothane: Stone dissolved to a great extent, with some small and a few larger insoluble fragments remaining.

MTBE: Same as for Halothane.

Pentafluoroacetophenone (for reference only): Stone did not dissolve.

Freon TF: Stone did not dissolve sufficiently to fragment over the observation time.

Freon TF with 5% methanol by volume: Stone dissolved with very small insoluble fragments remaining.

Freon TF with 7% ethanol by volume: Stone dissolved, very small insoluble fragments remaining.

Hexafluoro-1,1,3,4-tetrachlorobutane: Stone did not dissolve sufficiently to fragment.

Hexafluoro-1,1,3,4-tetrachlorobutane with 7% ethanol by volume: Stone dissolved, some medium sized fragments remaining.

Conclusion: Solvents which were shown to dissolve "synthetic gallstones" (i.e. melted cholesterol powder as described in Example 1) showed comparable ability to dissolve actual cholesterol-rich human gallstones. Also, addition of small amounts of lower alcohols, particularly ethanol, to the solvents improved solubility of cholesterol-rich human gallstones, just as it improved cholesterol solubility.

EXAMPLE 5

The procedure of Example 1 was repeated with a mixture of Halothane and MtBE and the results were as follows.

| Volume % Halothane in MtBE | Cholesterol Solubility | |
|---|---|---|
| | % by weight | grams/dl solvent |
| 0 | 24.7 | 24.4 |
| 5 | 23.4 | 24.1 |
| 10 | 21.1 | 22.6 |
| 20 | 17.0 | 19.7 |
| 30 | 14.1 | 17.7 |
| 40 | 11.1 | 14.7 |
| 50 | 9.8 | 14.1 |

Conclusion: At concentrations of Halothane up to 20-30 volume percent, the cholesterol solubility is still high. Above 30 volume percent of Halothane, the density of the solvent mixture exceeds that of most cholesterol-rich gallstones. The gallstones will tend to be displaced from the bile and float in or on the solvent mixture, thereby enhancing the cholesterol solubility rate. Further, the addition of Halothane to MtBE improves both the closed cup and open cup flash points and improves the combustion limits which results in the safer handling and use of MtBE.

EXAMPLE 6

The efficacy of Halothane as a solvent for in vivo dissolution of gallstones was demonstrated in the dog model. In each of two anaesthetized dogs, a mid-line abdominal laparatomy was performed and pre-weighed human gallstones (multiple stones weighing about 1 g total) were implanted directly into the gallbladder through a small incision in the fundus. A small single-lumen pigtail irrigation catheter was then inserted through the gallbladder incision and positioned, and the gallbladder incision was closed around the catheter with a purse-string suture. Small volumes (3.5 cc) of Halothane were alternately infused into and aspirated out of the gallbladder via the irrigation catheter at a rate of 6 cycles/minute for a period of eight hours. Upon completion of the Halothane irrigation, the dog was sacrificed and the gallbladder and cystic duct splayed open to retrieve any undissolved stone remnants. The stone remnants were weighed to assess the mass reduction resulting from Halothane irrigation. In the two dog studies, 96% and 99% respectively of the implanted stone masses were dissolved as a result of the Halothane irrigation.

Naturally, it will be understood that the above description and examples are to be taken by way of illustration and not by way of limitation. Modifications, equivalents, and other versions of the invention, which is defined in the appended claims will be apparent to those skilled in the art.

What is claimed is:

1. A method for dissolving cholesterol-rich calculus comprising contacting the calculus with a fluid compound of the formula R-X, R having 2 to 4 carbon atoms with substituents consisting of hydrogen or halogen, X being halogen, and wherein if X is fluorine, at least one substituent is selected from the group consisting of hydrogen, chlorine, bromine, or iodine.

2. The method of claim 1 and wherein R is alkyl.

3. The method of claim 1 and wherein R is cycloalkyl.

4. The method of claim 2 and wherein R-X is 2-bromo-2-chloro-1,1,1-trifluoroethane.

5. The method of claim 2 and wherein R-X is 2-chloro-1,2,-dibromo-1,1,2-trifluoroethane.

6. The method of claim 2 and wherein R-X is 1-bromo-2-chloro-1,1,2-trifluoroethane.

7. The method of claim 2 and wherein R-X is 2,3-dibromo-1,1,1-trifluoropropane.

8. The method of claim 2 and wherein R-X is 2-iodo-1,1,1-trifluoroethane.

9. The method of claim 2 and wherein R-X is 1,2-dichloro-1,1-difluoroethane.

10. The method of claim 3 and wherein R-X is 1,1,2-trichloro-2,3,3-trifluorocyclobutane.

11. The method of claim 2 and wherein R-X is hexafluoro-1,1,3,4,-tetrachlorobutane.

12. The method of claim 2 and wherein R-X is 1,1,1-trichlorotrifluoroethane.

13. The method of claim 2 and wherein R-X is 1,2-dibromo-tetrafluoroethane.

14. The method of claim 1 and wherein the cholesterol-rich calculus is a gallstone in the gallbladder.

15. The method of claim 1 and wherein the cholesterol-rich calculus is a gallstone or biliary duct stone in the biliary tract.

16. The method of claim 1 and wherein the cholesterol-rich calculus is plaque in the vascular system.

17. The method of claim 14 and wherein in vivo agitation of the compound and aspiration of bile and the compound is utilized to facilitate distribution of the compound and dissolution of the gallstone.

* * * * *